United States Patent
Mendoza et al.

(10) Patent No.: US 11,033,627 B2
(45) Date of Patent: Jun. 15, 2021

(54) METHOD FOR PRODUCING EXTENDED-RELEASE POTASSIUM CITRATE WAX MATRIX TABLET

(71) Applicants: Wendell G. Mendoza, Mandaluyong (PH); Rita Josefina M. Santos, Quezon (PH); Eulogio C. Singh, Rizal (PH); Kennie U. Dee, Quezon (PH)

(72) Inventors: Wendell G. Mendoza, Mandaluyong (PH); Rita Josefina M. Santos, Quezon (PH); Eulogio C. Singh, Rizal (PH); Kennie U. Dee, Quezon (PH)

(73) Assignee: Novex Science PTE. Limited, Gateway East (SG)

( * ) Notice: Subject to any disclaimer, the term of this patent is extended or adjusted under 35 U.S.C. 154(b) by 0 days.

(21) Appl. No.: 14/431,105

(22) PCT Filed: Sep. 27, 2012

(86) PCT No.: PCT/PH2012/000013
§ 371 (c)(1),
(2) Date: Mar. 25, 2015

(87) PCT Pub. No.: WO2014/051443
PCT Pub. Date: Apr. 3, 2014

(65) Prior Publication Data
US 2015/0231267 A1    Aug. 20, 2015

(51) Int. Cl.
*A61K 47/44* (2017.01)
*A61K 31/194* (2006.01)
*A61K 9/20* (2006.01)
*A61K 36/889* (2006.01)

(52) U.S. Cl.
CPC ............ *A61K 47/44* (2013.01); *A61K 9/2013* (2013.01); *A61K 9/2068* (2013.01); *A61K 9/2095* (2013.01); *A61K 31/194* (2013.01); *A61K 36/889* (2013.01)

(58) Field of Classification Search
CPC .... A61K 31/194; A61K 36/889; A61K 47/44; A61K 9/2013; A61K 9/2068; A61K 9/2095
See application file for complete search history.

(56) References Cited

U.S. PATENT DOCUMENTS

| 1,658,062 A | * | 2/1928 | Sprague | C11C 5/023 |
| | | | | 12/142 R |
| 4,966,776 A | | 10/1990 | Pak | |
| 6,132,772 A | | 10/2000 | Sherman | |
| 2008/0131504 A1 | | 6/2008 | Walsdorf, Sr. et al. | |

FOREIGN PATENT DOCUMENTS

EP    0295212 A2 * 12/1988    ........... A61K 9/1611

OTHER PUBLICATIONS

Reynhardt et al, Department of Physics, University of South Africa, 1988 . . . .*
Miyagawa et al, International Journal of Pharmaceutics, 138 (1998) 215-224.*
International Search Report—PCT/PH2012/000013—dated Apr. 30, 2013.

* cited by examiner

*Primary Examiner* — Jean P Cornet
(74) *Attorney, Agent, or Firm* — Benjamin C. Spehlmann

(57) ABSTRACT

The present invention relates to a method for producing extended-release potassium citrate tablet containing carnauba wax, wherein the method comprises heating the potassium citrate-carnauba wax mixture to a temperature below the temperature at which carnauba wax liquefies. This invention simplifies the production of extended release potassium citrate wax-matrix tablet.

16 Claims, No Drawings

METHOD FOR PRODUCING EXTENDED-RELEASE POTASSIUM CITRATE WAX MATRIX TABLET

CROSS-REFERENCE TO RELATED APPLICATIONS

This application is a U.S. National Stage application under 35 U.S.C. § 371 of International Application PCT/PH2012/000013 (published as WO 2014/051443 A1), filed Sep. 27, 2012. Benefit of the filing date of this application is hereby claimed. This application is hereby incorporated by reference in its entirety.

BACKGROUND OF THE INVENTION

Potassium citrate is used clinically to treat kidney stones by alkalizing the urinary pH and increasing urinary citrate concentration. However, its therapeutic efficacy is limited by its gastrointestinal complications such as irritation and ulcerations. Extended-release tablets of potassium citrate could minimize these side effects and have been shown to lead to sustained elevation of urinary pH and citrate concentration (Pak et al., 1984).

Considerable difficulties have been encountered in the preparation of extended-release matrix tablets containing potassium citrate. Potassium citrate is very soluble in water and the dosage required is very high. The only way to extend the release of potassium citrate tablet while keeping the tablet size acceptable for swallowing is to use a hydrophobic wax matrix, wherein the total amount of inactive ingredients is below 25% w/w.

Mission Pharmacal (San Antonio, Tex., USA) sells an extended-release potassium citrate tablet, Urocit-K, in three strengths: 5-meq, 10-meq, and 15-meq tablets. The daily dose of Urocit-K is 30-60 meq, which requires 6-12 tablets of the 5-meq, 3-6 tablets of the 10-meq, and 2-4 tablets of the 15-meq. Urocit-K is a wax matrix tablet containing potassium citrate, carnauba wax as extended-release agent, and magnesium stearate as, lubricant.

When the drug content is low, the carnauba wax can be dry mixed with the drug and other inactive ingredients prior to compression. For example, U.S. Pat. No. 4,904,478 teaches an extended-release wax matrix tablet of a highly water-soluble drug, sodium fluoride, wherein the carnauba wax, present at 35-70% w/w of the tablet weight, is dry mixed with the drug and other inactive ingredients prior to compression.

In the case of potassium citrate, because the drug dosage is high, the inactive ingredients including the extended-release agent(s) must be kept below 25% w/w to keep the tablet size acceptable for swallowing. If carnauba wax is used at less than 25% w/w, prior art teaches that the drug and carnauba wax should be heated until the carnauba wax liquefies, as described in Example 1 of US 2008/0131504 A1, to give an acceptable extended-release profile and abrasion. Abrasion is a measure of the durability of the tablet from the time it is compressed, to packaging, and to the time of use.

The process for making extended-release potassium citrate tablet containing carnauba wax is difficult. Heating until the carnauba wax liquefies requires a lot of time and then there is the problem of discharging the molten potassium citrate-carnauba wax mixture from the mixer. The cooled mass is extremely hard; therefore the molten mass must be poured into molds so that the cooled mixture is of appropriate size for feeding into a comminuting machine. There is a need for a simpler process to make extended-release potassium citrate wax matrix tablet.

SUMMARY OF THE INVENTION

We have surprisingly found that extended-release potassium citrate tablets containing carnauba wax can be produced without melting the wax. The potassium citrate-carnauba wax mixture is heated to a temperature below the temperature at which carnauba wax liquefies, and then discharged from the mixer as granules. The temperature is preferably higher than 55° C., and most preferably higher than 60° C. The cooled granulate can then be fed directly into a comminuting machine for size reduction. The tablet of this instant invention has the same dissolution profile as prior art tablet produced by totally melting the wax. This instant invention reduces the production time and eliminates the complexities related to melting and cooling the wax.

DETAILED DESCRIPTION OF THE INVENTION

Extended-release potassium citrate tablet must comply with USP 35. Dissolution is performed in 900 ml water, apparatus 2 at 50 rpm, and must comply with the following dissolution specifications:

TABLE 1

| (dissolution, 12 units) | | |
|---|---|---|
| Time | All Units | Average |
| 30 min | 30-60% | 35-55% |
| 1 hour | 45-75% | 50-70% |
| 3 hour | ≥75% | ≥80% |

Abrasion was measured in an Erweka TAR20. Briefly, ten tablets were placed inside a baffled 190 mm ID drum. The drum was rotated at 25 rpm for 4 minutes. The difference in the total tablet weight before and after rotating the drum divided by the initial tablet weight is the abrasion. The desired abrasion for extended-release potassium citrate tablet is not more than 1.5%.

COMPARATIVE EXAMPLE 1

10-meq tablets of Urocit-K (Mission Pharmacal, lot 9L038) were purchased. The tablet hardness was 9 kp, and abrasion was 0.3%. The dissolution was performed according to USP 35. The result is as follows:

TABLE 2

| (dissolution, 12 units) | | |
|---|---|---|
| Time | Range | Average |
| 30 min | 43.6-47.6% | 45.2% |
| 1 hour | 57.9-61.1% | 60.4% |
| 3 hour | 87.9-97.4% | 91.7% |

The product complies with the USP 35 requirement for extended-release potassium citrate tablet.

EXAMPLE 2

A 10-meq tablet was prepared by dry mixing potassium citrate and carnauba wax. The formulation is given in Table 3.

TABLE 3

| Ingredient | mg/tablet | % w/w |
|---|---|---|
| Tripotassium citrate monohydrate | 1080 | 85 |
| Carnauba wax | 177 | 14 |
| Magnesium stearate | 13 | 1 |

Potassium citrate was sieved through mesh 18, and then mixed with carnauba wax for 5 minutes in a sigma mixer. Magnesium stearate was passed through mesh 30, added to the potassium citrate-carnauba wax mixture, and mixed for 1 minute. The granule was compressed into 18.9×8.6 mm elliptical tablet in a Stokes-Pennwalt rotary tablet press model 900. Tablet hardness was 7 kp, and the abrasion of the tablet was 1.8%, which is not acceptable. The dissolution profile is as follows:

TABLE 4

| (dissolution, 12 units) | | |
|---|---|---|
| Time | Range | Average |
| 30 min | 47.8-62.0% | 53.7% |
| 1 hour | 66.9-74.9% | 68.5% |
| 3 hour | 89.7-95.6% | 92.7% |

The product fails the dissolution requirement of USP 35. This example illustrates that dry mixing carnauba wax at 14% w/w to produce granules for direct compression does not produce tablet that complies with the USP requirements for potassium citrate extended-release tablet. Further, the abrasion is not acceptable.

EXAMPLE 3

A 10-meq tablet was prepared by dry mixing potassium citrate and carnauba wax. The formulation is given in Table 5.

TABLE 5

| Ingredient | mg/tablet | % w/w |
|---|---|---|
| Tripotassium citrate monohydrate | 1080 | 79 |
| Carnauba wax | 272 | 20 |
| Magnesium stearate | 14 | 1 |

Potassium citrate was sieved through mesh 18, and then mixed with carnauba wax for 5 minutes in a sigma mixer. Magnesium stearate was passed through mesh 30, added to the potassium citrate-carnauba wax mixture, and mixed for 1 minute. The granule was compressed into 18.9×8.6 mm elliptical tablet in a Stokes-Pennwalt rotary tablet press model 900. Tablet hardness was 7 kp, and the abrasion of the tablet was 2%, which is not acceptable. The dissolution profile is as follows:

TABLE 6

| (dissolution, 12 units) | | |
|---|---|---|
| Time | Range | Average |
| 30 min | 49.4-54.5% | 52.5% |
| 1 hour | 64.3-69.1% | 67.1% |
| 3 hour | 90.2-94.5% | 92.4% |

This example illustrates that dry mixing carnauba wax at 20% w/w to produce granules for direct compression, while passing the compendial dissolution requirement, does not produce tablet of acceptable abrasion.

EXAMPLE 4

A 10-meq tablet with the same formulation as Example 2 was prepared by fully melting the carnauba wax. The procedure is as follows:
1. The potassium citrate was comminuted in a Fitzmill D6, knives forward, using perforated screen mesh 8.
2. The comminuted potassium citrate from #1 was mixed with carnauba wax in a sigma mixer for 20 minutes.
3. The granule from #2 was comminuted in a Fitzmill D6, knives forward, using perforated screen mesh 12.
4. The granule from #3 was heated in a jacketed sigma mixer, with continued mixing. Heating was continued until the carnauba wax was fully melted (above 80° C.), and for an additional 10 minutes thereafter.
5. The liquid mass from #4 was poured into 2"×2"×2" molds, and allowed to cool to room temperature.
6. The blocks from #5 were comminuted in a Fitzmill D6, knives forward, using perforated screen mesh 16.
7. Magnesium stearate was passed through mesh 30 and mixed with the comminuted granule of #6 in a sigma mixer for 2 minutes.
8. The granule from #7 was compressed into 18.9×8.6 mm elliptical tablet in a Stokes-Pennwalt rotary tablet press model 900.

Tablet hardness was 12 kp, and the abrasion of the tablet was 0.5%. The dissolution profile is as follows:

TABLE 7

| (dissolution, 12 units) | | |
|---|---|---|
| Time | Range | Average |
| 30 min | 46.8-53.3% | 48.2% |
| 1 hour | 61.7-69.1% | 63.1% |
| 3 hour | 91.3-98.3% | 92.7% |

This tablet produced according to prior art method has good abrasion and passes the dissolution requirement of USP 35.

EXAMPLE 5

A 10-meq tablet of this instant invention was prepared. The formulation is the same as Example 2. The procedure is as follows:
1. The potassium citrate was comminuted in a Fitzmill D6, knives forward, using perforated screen mesh 8.
2. The comminuted potassium citrate from #1 was mixed with carnauba wax in a sigma mixer for 20 minutes.
3. The granule from #2 was comminuted in a Fitzmill D6, knives forward, using perforated screen mesh 12.
4. The granule from #3 was heated in a jacketed sigma mixer, with continued mixing. Heating was continued until the temperature reached 70° C., which is below the melting point of carnauba wax.
5. The granule from #4 was discharged into plastic drums and allowed to cool to room temperature.
6. The cooled granule from #5 was comminuted in a Fitzmill D6, knives forward, using perforated screen mesh 16.
7. Magnesium stearate was passed through mesh 30 and mixed with the comminuted granule of #6 in a sigma mixer for 2 minutes.

8. The granule from #7 was compressed into 18.9×8.6 mm elliptical tablet in a Stokes-Pennwalt rotary tablet press model 900.

Tablet hardness was 12 kp, and the abrasion of the tablet was 0.6%. The dissolution profile is as follows:

TABLE 8

(dissolution, 12 units)

| Time | Range | Average |
|---|---|---|
| 30 min | 43.5-48.7% | 46.8% |
| 1 hour | 59.6-63.8% | 61.9% |
| 3 hour | 89.9-94.7% | 92.8% |

The tablet produced according to this instant invention has good abrasion and similar dissolution profile with tablets produced using prior art method whereby the carnauba wax is fully melted (Example 4). This is surprising because it was previously believed that extended-release potassium citrate tablet containing carnauba wax can only be produced by fully melting the carnauba wax. The method of this instant invention significantly simplifies the production of extended-release potassium citrate tablet, with reduction in production time and elimination of manufacturing complexities related to melting and cooling the wax.

COMPARATIVE EXAMPLE 6

15-meq tablets of Urocit-K (Mission Pharmacal, lot 2A012) were purchased. The tablet hardness was 12 kp, and abrasion was 1%. The dissolution was performed according to USP 35. The result is as follows:

TABLE 9

(dissolution, 12 units)

| Time | Range | Average |
|---|---|---|
| 30 min | 35.2-40.2% | 38.0% |
| 1 hour | 49.9-61.0% | 53.1% |
| 3 hour | 79.7-82.8% | 81.1% |

The product complies with the USP 35 requirement for extended-release potassium citrate tablet.

EXAMPLE 7

A 15-meq tablet was prepared by fully melting the carnauba wax. The formulation is given in Table 10.

TABLE 10

| Ingredient | mg/tablet | % w/w |
|---|---|---|
| Tripotassium citrate monohydrate | 1620 | 84 |
| Carnauba wax | 289 | 15 |
| Magnesium stearate | 19 | 1 |

The tablets were made as described in Example 4 except that the granule was compressed into 22.5×9.3 mm elliptical tablets with a hardness of 13 kp and abrasion of 0.3%. The dissolution is as follows:

TABLE 11

(dissolution, 12 units)

| Time | Range | Average |
|---|---|---|
| 30 min | 35.9-41.2% | 38.5% |
| 1 hour | 48.9-62.0% | 53.5% |
| 3 hour | 79.5-84.6% | 82.2% |

This tablet produced according to prior art method has good abrasion and passes the dissolution requirement of USP 35.

EXAMPLE 8

A 15-meq tablet of this instant invention was prepared. The formulation is the same as Example 7. The procedure is as follows:
1. The potassium citrate was comminuted in a Fitzmill D6, knives forward, using perforated screen mesh 8.
2. The comminuted potassium citrate from #1 was mixed with carnauba wax in a sigma mixer for 20 minutes.
3. The granule from #2 was comminuted in a Fitzmill D6, knives forward, using perforated screen mesh 12.
4. The granule from #3 was heated in a jacketed sigma mixer, with continued mixing. Heating was continued until the temperature reached 60° C., which is below the melting point of carnauba wax.
5. The granule from #4 was discharged into plastic drums and allowed to cool to room temperature.
6. The cooled granule from #5 was comminuted in a Fitzmill D6, knives forward, using perforated screen mesh 16.
7. Magnesium stearate was passed through mesh 30 and mixed with the comminuted granule of #6 in a sigma mixer for 2 minutes.
8. The granule from #7 was compressed into 22.5×9.3 mm elliptical tablet in a Stokes-Pennwalt rotary tablet press model 900.

Tablet hardness was 12 kp, and the abrasion of the tablet was 0.8%. The dissolution profile is as follows:

TABLE 12

(dissolution, 12 units)

| Time | Range | Average |
|---|---|---|
| 30 min | 38.8-41.0% | 40.1% |
| 1 hour | 53.1-56.3% | 55.0% |
| 3 hour | 84.7-90.9% | 87.6% |

The tablet produced according to this instant invention has good abrasion and passes the USP 35 dissolution specs. This is surprising because it was previously believed that extended-release potassium citrate tablet containing carnauba wax can only be produced by fully melting the carnauba wax. The method of this instant invention significantly simplifies the production of extended-release potassium citrate tablet, with reduction in production time and elimination of manufacturing complexities related to melting and cooling the wax.

The invention claimed is:
1. A method for preparing an extended-release potassium citrate tablet containing carnauba wax, the method comprising:
   a) mixing potassium citrate and carnauba wax at a mixing temperature of at least 55° C., b) cooling the mixture obtained in step a), and
c) forming the extended-release potassium citrate tablet from the cooled mixture obtained in step b),
wherein the mixing temperature during mixing step (a) does not exceed 80° C., wherein the tablet is prepared without exceeding the melting temperature of the carnauba wax, wherein the amount of carnauba wax is less than 25% w/w of the tablet weight, and
wherein the extended-release potassium citrate tablet consists of the potassium citrate and carnauba wax, and a lubricant.

2. The method according to claim 1 wherein the mixing temperature is 60° C. or higher.

3. The method according to claim 2 wherein mixing temperature is 65° C. or higher.

4. The method according to claim 1 wherein, following cooling step b), the cooled mixture is comminuted, and mixed with the lubricant prior to forming the extended-release potassium citrate tablet in step (c).

5. The method according to claim 1, wherein the carnauba wax is less than 20% w/w of the tablet weight.

6. The method according to claim 5, wherein the carnauba wax is less than 15% w/w of the tablet weight.

7. The method according to claim 4, wherein the abrasion of the tablet is less than 1.5%.

8. The method according to claim 7, wherein the abrasion of the tablet is less than 1%.

9. A method of making extended-release potassium citrate tablet containing carnauba wax, comprising the following steps:
a) Mixing and heating potassium citrate and carnauba wax to 55° C. or higher, but below the melting temperature of the carnauba wax to obtain granules of the potassium citrate and carnauba wax;
b) Cooling and comminuting the granules obtained in step a);
c) Mixing a lubricant into the comminuted granules obtained in step b); and
d) Compressing the mixture obtained in step c) into said tablets containing the carnauba wax in an amount of less than 25% w/w, and having an abrasion of less than 1.5%,
wherein the tablets are prepared without exceeding the melting temperature of the carnauba wax,
and further wherein the extended-release potassium citrate tablets consist of the potassium citrate, the carnauba wax, and the lubricant.

10. The method according to claim 9 wherein step a) comprises mixing and heating the potassium citrate and carnauba wax to 60° C. or higher.

11. The method according to claim 10 wherein step a) comprises mixing and heating the potassium citrate and carnauba wax to 65° C. or higher.

12. The method according to claim 11, wherein the amount of the carnauba wax contained in the tablets is less than 20% w/w.

13. The method according to claim 12, wherein the amount of the carnauba wax contained in the tablets is less than 15% w/w.

14. The method of claim 9, wherein cooling and comminuting in step b) are performed without transferring the granules obtained in step a) to a mold.

15. The method of claim 1, wherein the potassium citrate and the carnauba wax are present in the extended-release potassium citrate tablet in a combined amount of at least 99% w/w.

16. The method of claim 9, wherein the lubricant is magnesium stearate.

* * * * *